US008845522B2

(12) United States Patent
McIntyre et al.

(10) Patent No.: US 8,845,522 B2
(45) Date of Patent: Sep. 30, 2014

(54) MEDICAL INSTRUMENT WITH A DEFLECTABLE DISTAL PORTION

(75) Inventors: Jon T. McIntyre, Newton, MA (US); Jessica Hixon, Watertown, MA (US); Isaac Ostrovsky, Wellesley, MA (US); Jozef Slanda, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1518 days.

(21) Appl. No.: 12/191,485

(22) Filed: Aug. 14, 2008

(65) Prior Publication Data
US 2009/0069632 A1    Mar. 12, 2009

Related U.S. Application Data

(60) Provisional application No. 60/971,114, filed on Sep. 10, 2007.

(51) Int. Cl.
*A61B 1/00* (2006.01)
*A61B 1/005* (2006.01)
*A61B 1/04* (2006.01)

(52) U.S. Cl.
CPC ........... *A61B 1/0055* (2013.01); *A61B 1/00098* (2013.01); *A61B 1/0052* (2013.01)
USPC ............................. 600/146; 600/130; 600/129

(58) Field of Classification Search
CPC .. A61B 1/0051; A61B 1/0052; A61B 1/0053; A61B 1/0057
USPC ......... 600/114, 139–142, 146, 148–150, 182, 600/151
See application file for complete search history.

(56) References Cited

U.S. PATENT DOCUMENTS

| | | | | |
|---|---|---|---|---|
| 3,470,876 A | * | 10/1969 | Barchilon | 604/95.04 |
| 3,572,325 A | * | 3/1971 | Bazell et al. | 600/141 |
| 4,203,430 A | | 5/1980 | Takahashi | |
| 4,546,761 A | | 10/1985 | McCullough | |
| 4,799,474 A | * | 1/1989 | Ueda | 600/151 |
| 4,852,565 A | | 8/1989 | Eisele | |
| 5,005,558 A | | 4/1991 | Aomori | |
| 5,152,748 A | * | 10/1992 | Chastagner | 604/95.05 |
| 5,271,382 A | | 12/1993 | Chikama | |
| 5,477,856 A | | 12/1995 | Lundquist | |
| 5,702,754 A | | 12/1997 | Zhong | |
| 5,857,964 A | | 1/1999 | Konstorum et al. | |

(Continued)

FOREIGN PATENT DOCUMENTS

EP    1 174 077 A1    1/2002
WO   WO 2005/079683 A1    9/2005

OTHER PUBLICATIONS

Notification of Transmittal of the International Search Report and the Written Opinion of the International Searching Authority, or the Declaration issued in corresponding international application No. PCT/US2008/073106, mailed Oct. 27, 2008.

*Primary Examiner* — Alireza Nia
(74) *Attorney, Agent, or Firm* — Bookoff McAndrews, PLLC

(57) ABSTRACT

A deflection assembly of a medical instrument (such as an endoscope or a flexible ureteroscope) allows an operator to deflect a distal portion of the instrument using one or more controls located at a proximal portion of the instrument. The instrument allows the operator to achieve multi-directional deflection of the distal portion.

20 Claims, 5 Drawing Sheets

(56) References Cited

U.S. PATENT DOCUMENTS

| | | |
|---|---|---|
| 5,873,817 A | 2/1999 | Kokish et al. |
| 5,938,588 A | 8/1999 | Grabover et al. |
| 6,048,620 A | 4/2000 | Zhong |
| 6,171,235 B1 | 1/2001 | Konstorum et al. |
| 6,450,948 B1 | 9/2002 | Matsuura et al. |
| 6,475,140 B1 | 11/2002 | Konstorum et al. |
| 6,485,411 B1 | 11/2002 | Konstorum et al. |
| 6,524,274 B1 * | 2/2003 | Rosenthal et al. ......... 604/96.01 |
| 6,656,195 B2 | 12/2003 | Peters et al. |
| 6,740,030 B2 | 5/2004 | Martone et al. |
| 6,749,560 B1 | 6/2004 | Konstorum et al. |
| 6,780,151 B2 | 8/2004 | Grabover et al. |
| 6,790,173 B2 | 9/2004 | Saadat et al. |
| 6,817,974 B2 | 11/2004 | Cooper et al. |
| 6,858,005 B2 | 2/2005 | Ohline et al. |
| 6,890,329 B2 | 5/2005 | Carroll et al. |
| 7,090,637 B2 | 8/2006 | Danitz et al. |
| 7,678,117 B2 * | 3/2010 | Hinman et al. ............... 606/108 |
| 2004/0186350 A1 | 9/2004 | Brenneman et al. |
| 2004/0199052 A1 | 10/2004 | Banik et al. |
| 2004/0225186 A1 | 11/2004 | Horne, Jr. et al. |
| 2004/0236316 A1 | 11/2004 | Danitz et al. |
| 2005/0015072 A1 | 1/2005 | Engel et al. |
| 2005/0090809 A1 | 4/2005 | Cooper et al. |
| 2005/0096694 A1 | 5/2005 | Lee |
| 2005/0107667 A1 | 5/2005 | Danitz et al. |
| 2005/0119644 A1 | 6/2005 | Koerner |
| 2005/0131279 A1 | 6/2005 | Boulais et al. |
| 2005/0182475 A1 | 8/2005 | Jen et al. |
| 2005/0273084 A1 | 12/2005 | Hinman et al. |
| 2005/0273085 A1 | 12/2005 | Hinman et al. |
| 2006/0041188 A1 | 2/2006 | Dirusso et al. |
| 2006/0094931 A1 | 5/2006 | Danitz et al. |
| 2006/0111209 A1 | 5/2006 | Hinman et al. |
| 2006/0111210 A1 | 5/2006 | Hinman |
| 2006/0111615 A1 | 5/2006 | Danitz et al. |
| 2006/0111616 A1 | 5/2006 | Danitz |

* cited by examiner

MEDICAL INSTRUMENT WITH A DEFLECTABLE DISTAL PORTION

CROSS-REFERENCE TO RELATED CASES

This application claims priority to, and the benefit of Provisional U.S. Patent Application Ser. No. 60/971,114, filed Sep. 10, 2007, the entirety of which is incorporated herein by reference.

TECHNICAL FIELD

This disclosure relates to flexible medical instruments, in particular instruments with deflectable distal portions. One embodiment of such an instrument can be a flexible ureteroscope or some other type of flexible scope used to visualize and/or get access to some internal portion(s) of a patient's body using minimally invasive techniques.

BACKGROUND INFORMATION

An endoscope or other type of scope for use in medical applications generally is a medical instrument with a shaft with optics (such as one or more fiber optic cables) that carries light to and from the interior of a patient's body to allow an operator of the scope to visualize that interior. A scope typically is used by an operator during a minimally invasive medical procedure, in which a distal portion of the scope is inserted into the patient's body through a natural orifice of the patient's body or through a small incision made in the patient to gain access to the patient's interior. A scope typically has one or more working channels extending through the proximal handle and through the shaft to the distal end of the scope. The channel(s) can carry medication, fluids, air, and/or surgical instruments. A scope can be used in minimally invasive procedures requiring visualization of, access to, and treatment of one or more interior portions of a patient's body such as the gastrointestinal tract, nasal cavity, sinuses, pharynx, tracheobronchial system, genitourinary tract, uterus, peritoneal cavity, pleural cavity, and subfascial spaces.

Various mechanisms for deflecting the distal portion of a scope or other medical instrument are known. Pull wires or cords running along the shaft of the instrument can be used to bend the distal portion. Such pull wire or cord arrangements tend to pull the distal portion of the instrument in a non-planar direction and cause one or more other portions of the shaft of the instrument to buckle or form a series of "S" shapes from the tension of the pull wires or cords. Also, integral pull-wire deflection arrangements may require the user to turn or twist the entire shaft to obtain additional degrees of freedom of movement of the distal portion. This kind of rotational movement can alter an image in undesirable ways.

SUMMARY

In the disclosed embodiments of a medical instrument with a deflectable distal portion, the instrument has a handle and a shaft and can be some type of scope such as a flexible ureteroscope. The flexible ureteroscope can be made inexpensively enough, in accordance with the invention, such that it can be a single-use medical device that must be disposed of after that single use. The very distal tip or end of the shaft can be deflected, or more typically a distal portion of the shaft can be bent or deflected to alter the position of the distal end of the shaft. This allows an operator to view and access areas of the patient's interior beyond those possible with a fixed, straight, and non-deflectable instrument.

A medical instrument according to the invention can have a multi-directional deflectable distal portion. A deflection assembly (that is part of or a sub-assembly of the medical instrument, for example) can be used to achieve this deflection capability.

In one embodiment, a medical instrument according to the invention includes a handle and a shaft extending from the handle where at least a portion of the shaft (such as a distal portion of the shaft) is deflectable in at least one and possibly multiple directions off of an axis running longitudinally down the shaft of the instrument. One, two, or more elongated deflection members can be disposed within the shaft, and can be moved independent of the shaft. For example, the deflection member(s) can be located in an annular space formed between an outer tube of the shaft that is concentric with a multi-lumen inner tube of the shaft. If two deflection members are employed as a deflection assembly, each of the two members can transition from a half-tube that extends through most of the length of the shaft in the annular space to a tapering section in the distal portion of the shaft and finally to a ring within the annular space at or near the distal end of the shaft. Formed integrally with, or connected to in some manner, a proximal end of each of the half-tubes can be structure at or near the handle that allows an operator of the instrument to grasp and manipulate with one or both hands to actuate the deflection members and thereby cause deflection of the distal portion of the shaft.

In one aspect, the invention generally relates to a medical instrument comprising a handle, an outer elongated member extending distally from the handle, an inner elongated member within at least a portion of the outer elongated member such that the arrangement of the outer and inner members defines a space therebetween, and a deflection assembly disposed within at least some of the space. The deflection assembly can be manipulated by a user of the instrument to deflect a distal portion of the outer and inner members in at least one of at least two possible directions off of a longitudinal axis running the length of the outer and inner tubes. The deflection assembly can comprise at least two elements, one or more of which can include a tapered section.

BRIEF DESCRIPTION OF THE DRAWINGS

For a fuller understanding of the nature and operation of various embodiments according to the present invention, reference is made to the following description taken in conjunction with the accompanying drawing figures wherein like reference characters denote corresponding parts throughout the several views.

DESCRIPTION

Figure 1:
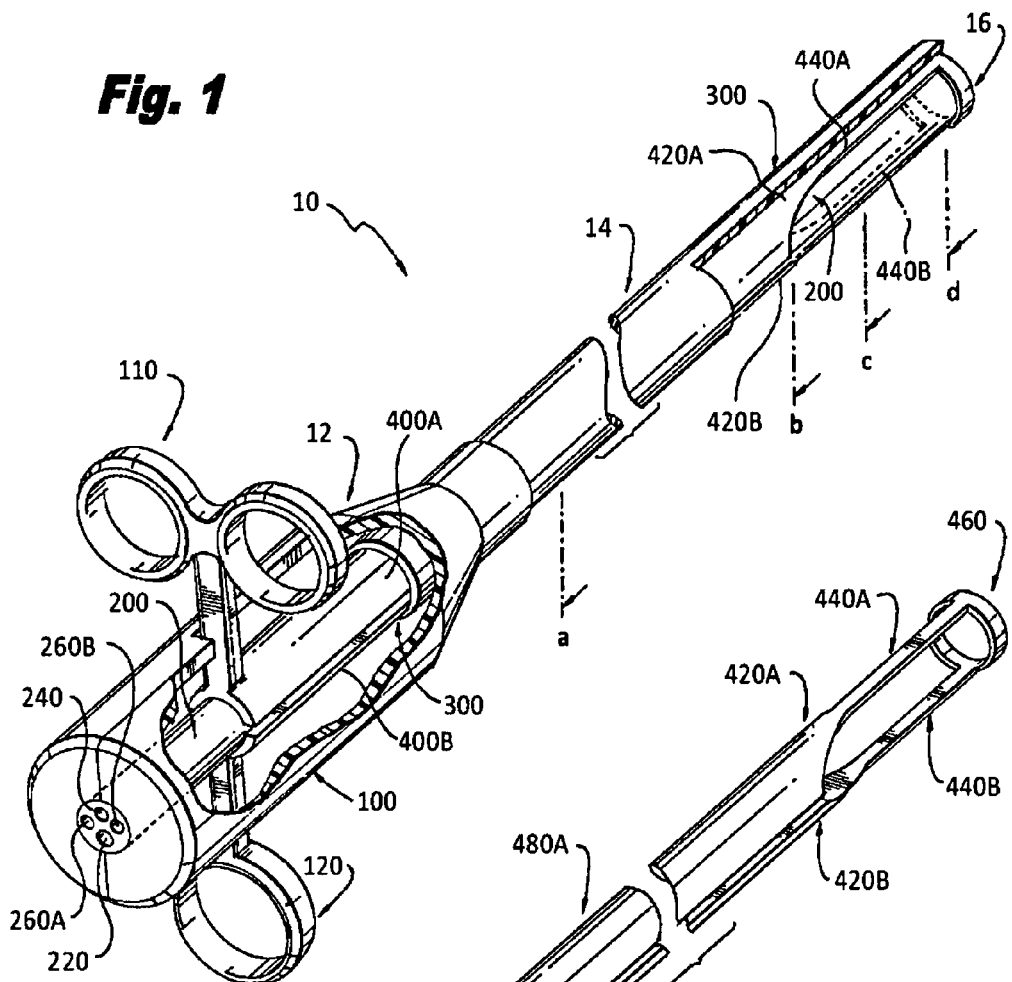
FIG. 1 is a partial cutaway view of an endoscope incorporating the invention, showing the proximal (handle) end and the distal (shaft) end. The deflection assembly and finger/thumb grips are visible in the cutaway view.

As indicated above, the present invention relates to flexible medical instruments, in particular instruments with deflectable distal portions such as, for example, endoscopes, ureteroscopes, and catheters. These medical devices allow an operator to access and view internal body anatomy of a patient as well as to insert surgical instruments such as biopsy forceps, graspers, baskets, snares, fulguration probes, and other tools into the patient's body. In addition, these devices may include integrated diagnostic and therapeutic capabilities to allow the operator to treat the patient in a single procedure.

At least a distal portion of a shaft of a medical instrument can be bended or deflected. The instrument can be an endoscope, a ureteroscope, or any other type of scope, for example. One disclosed embodiment involves two half-tube structures. The half-tubes extend from the proximal (handle) portion of the instrument toward the distal portion of the instrument and taper at some point along the shaft in or around the distal portion. The terms proximal and distal require a point of reference. In this application, the point of reference is the perspective of the user. Therefore, the term proximal will always refer to an area closest to the user, whereas distal will always refer to an area away from the user. The half-tubes can be located in an annular space formed by two concentric tubes comprising the shaft of the instrument. The outer tube acts as a protective cover for the shaft of the instrument and can be constructed of a flexible polymer. The inner tube can have multiple lumens, and one or more of those multiple lumens can contain one or more optical fibers. One or more of the multiple lumens can be a working channel for accepting a surgical or other instrument and/or for allowing fluids or other material to be transported therethrough. The inner surface of the outer tube, and the outer surface of the multi-lumen inner tube can be constructed of material with a low coefficient of friction. At or near the distal portion of the shaft of instrument, where active bending or deflection is desired, each half-tube transitions to a narrower relatively flat deflection member that extends distally and attaches to an attachment ring within the annular space near the distal end of the instrument. The half-tubes together with their tapered sections and the ring at the distal end can constitute a deflection assembly. The deflection assembly is movable longitudinally, at least to some degree, within the annular space, and each of the half-tube structures can be pushed and/or pulled longitudinally to move one or both of them (in the same longitudinal direction or in opposite longitudinal directions) to some degree, but they also are restricted in their longitudinal movement given that the distal end of each structure is attached in some manner (e.g., hinged, ball-and-socket, pivot point, welded, adhered, etc.) to the ring. Such an arrangement can prevent buckling of the shaft and can prevent rotational movement of the distal end of the shaft, and it provides robust distal portion deflection performance at a reasonable manufacturing cost. Such an arrangement can result in a low cost deflectable scope that can then be designated as single-use and/or disposable.

In FIG. 1, the depicted medical instrument or device is a flexible fiberoptic scope 10 that includes a handle 12 for grasping and controlling the instrument, an elongated shaft 14, and a tip 16. Embodiments of the instrument can have shafts of varying length, from about 6 cm. to about 165 cm., for example. The handle 12 has a housing 100 that contains the proximal end of a multi-lumen inner tube 200. The multi-lumen inner tube 200 extends along the shaft 14 and terminates at the tip 16. The proximal end of an outer tube 300 originates at the distal end of the handle 12, extends along the shaft 14 and terminates at the tip 16. The housing 100 also contains the proximal ends of half-tubes 400A and 400B, located outside the multi-lumen inner tube 200 and inside the outer tube 300. The half-tubes extend within the shaft 14, and near the distal end of the shaft taper in width and flatten as transition structures 420A and 420B, ultimately resulting in narrower and approximately flat deflection members 440A and 440B (hereinafter designated as deflection members 440A and 440B). The deflection members 440A and 440B attach to an attachment ring 460 at opposite points on the ring. Finger grips 110 and thumb grip 120 are connected to the proximal ends of the half-tubes 400A and 400B. Within the multi-lumen inner tube 200 are a lumen 220 that in one embodiment may be used to introduce surgical instruments to the tip 16 of the instrument. In other embodiments, the lumen 220 may be used to administer drugs, or add or withdraw fluids or gases. A channel 240 is also present within the multi-lumen inner tube 200 for carrying an optical fiber or an electronic cable for transmission of image data received at the tip 16. In one embodiment, channels 260A and 260B are also present within the multi-lumen inner tube 200 for carrying optical fibers to illuminate the field of view in the vicinity of the tip 16.

Figure 2:
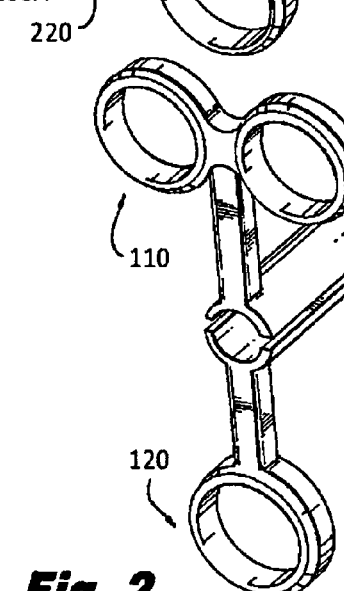
FIG. 2 is a side perspective view of the deflection assembly of FIG. 1 seen in isolation, connected proximally to the finger and thumb grips of the instrument.

In FIG. 2, the deflection assembly 480A and 480B and finger and thumb grips of the disclosed embodiment are seen in isolation. The finger grips 110 and thumb grip 120 are connected to the proximal end of the half-tubes 400A and 400B by any suitable means, including screws or weld joints.

In other embodiments, the finger grips 110 and thumb grip may be formed integrally with the proximal ends of the half-tubes 400A and 400B. The half-tubes extend along most of the length of the shaft 14 of the instrument. At a location along the length of the shaft 14 of the instrument, the half-tubes taper or transition to narrower and flatter structures 420A and 420B. At a point near the distal end of the shaft 14 of the instrument, where bending of the shaft 14 of the instrument is desired, the distal deflection members 440A and 440B are narrow and approximately flat. The characteristics of the materials that comprise the distal deflection members 440A and 440B will determine how flat and narrow they can be made. The deflection member's moment of inertia (I) determines how flat it must be to provide a preferential bending plane. Stiffer materials will require them to be flatter and narrower. The length of the distal deflection members 440A and 440B is determined by the amount of the distal end of the shaft 14 that one wishes to make bendable. The distal deflection members 440A and 440B are attached to an attachment ring 460, that is located near the tip of the shaft 14 of the instrument, and lies within the annular space between the multi-lumen inner tube 200 and the outer tube 300. In the disclosed embodiment, the two nearly semicircular half-tubes 400A and 400B are located opposed to each other, resulting in attachment of the distal deflection members 440A and 440B at points 180 degrees apart on the attachment ring 460. The curvature of the half-tubes imparts additional rigidity to the deflection assembly 480A and 480B to prevent buckling of the shaft 14 of the instrument in areas proximal to the desired bending region.

Figure 3:
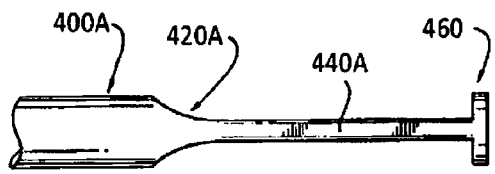
FIG. 3 is a top view of the deflection assembly of FIG. 1 seen in isolation, showing how the half-tube tapers to a flat member at the distal end, ultimately attaching to an attachment ring.

In FIG. 3, a top view of the half-tube 400A, transition structure 420A, and distal deflection member 440A shows that the transition structure 420A is relatively short. In another embodiment, the transition structure 420A can be longer in order to lengthen the bending characteristics of the deflection assembly 480A. A longer transition can, for example, cause the bending action to start at the distal end and 'roll' back to the proximal end as more deflection is imparted by the longitudinal movement of the half-tube 400A. The distal deflection member 440A is sufficiently narrow to eliminate the resistance to bending engendered by the curved profile of the half-tube 400A. It is sufficiently flat to enforce bending of the tip 16 of the instrument in only one plane. The proximal half-tubes 400A and 400B also help to prevent bending of the tip 16 of the instrument in more than one plane, and help to prevent rotational movement of a camera or lens embedded within the multi-lumen inner tube 200 at the tip 16 of the instrument.

Figure 4:
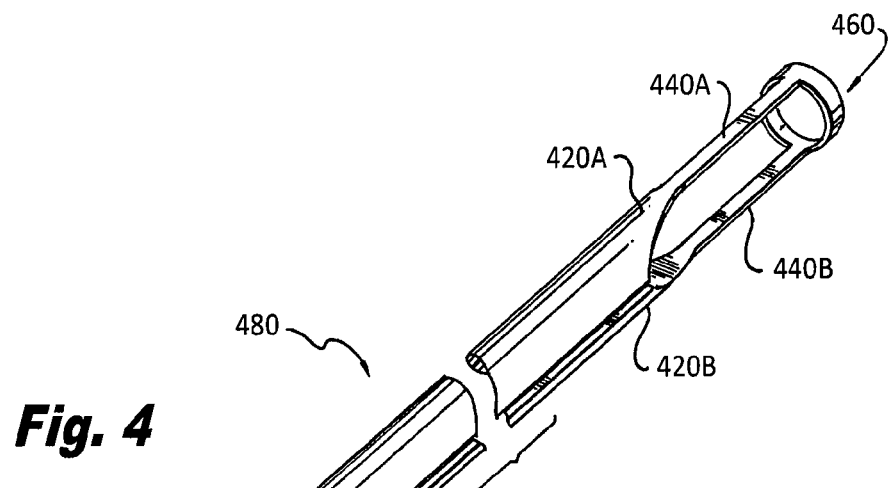
FIG. 4 is a side perspective view of the deflection assembly of FIG. 1 seen in isolation, showing the proximal half-tubes, the distal flat members, and an attachment ring.

In FIG. 4, the deflection assembly 480 of the disclosed embodiment consists of the half-tubes 400A and 400B, the transition structures 420A and 420B, the deflection members 440A and 440B, and the attachment ring 460. In one embodiment, the half-tubes 400A and 400B and the deflection members 440A and 440B are made from the same material, such as stainless steel or Nitinol (which is a Nickel-Titanium alloy). In other embodiments, they may be made from a rigid polymer such as polyimide, polystyrene, polycarbonate, high density polyethylene, ABS and others. In another embodiment, the deflection members 440A and 440B are made from flexible material such as Nitinol, and attached to the half-tubes 400A and 400B made from stainless steel, the attachment occurring within or at the distal end of the transition structures 420A and 420B. The surface of the materials comprising the half-tubes 400A and 400B and the deflection members 440A and 440B preferably have a low coefficient of friction to facilitate the movement of the deflection assembly 480 within the shaft 14 of the instrument.

Similarly the inner surface of the outer tube 300 and the outer surface of the multi-lumen inner tube 200 are preferably made of materials with a low coefficient of friction. In the disclosed embodiment, metal surfaces are preferably polished or coated. When polymers are used, coatings may be applied to their surfaces to make them more slippery. The outer surface of the multi-lumen inner tube 200 may be made, for example, of polytetrafluoroethylene (PTFE), fluoroethylene-propylene (FEP), perfluoralkoxy (PFA), and other fluoropolymers, as well as polyethylene, polypropylene and others. The outer tube 300 can be made, for example, of a flexible polymer such as polyurethane or linear low density polyethylene (LLDPE). Preferably, the compound used is extrudable, to allow for more efficient manufacture of the tube.

Figure 5:
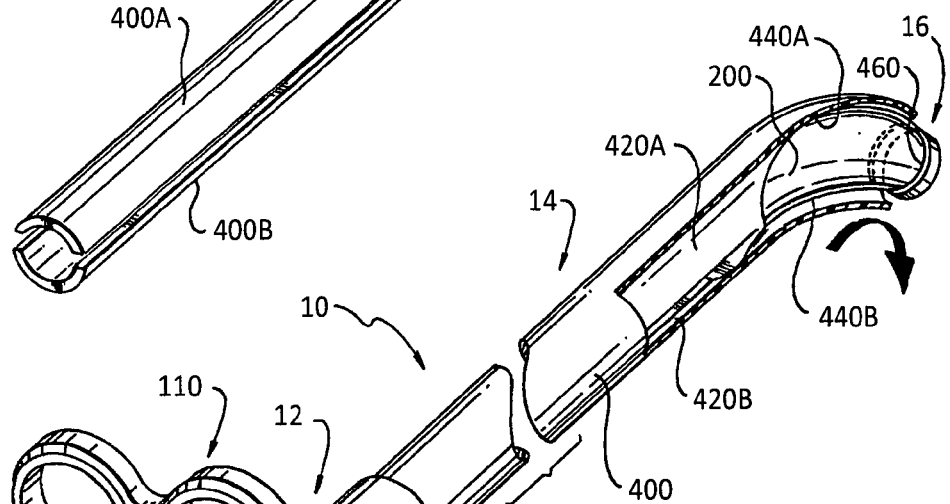
FIG. 5 shows the operation of the deflection assembly of FIG. 1 within the endoscope, with the top half-tube advanced distally and the bottom half-tube pulled proximally, resulting in downward deflection of the distal shaft of the endoscope.

In FIG. 5, the distal end of the shaft 14 of the instrument 10 can be made to bend downward by pulling the thumb grip 120 in a proximal direction, causing the half-tube 400B to slide proximally and pull against the lower part of the attachment ring 460. The distal deflection member 440B is sufficiently flat and narrow to flex and cause the adjacent portion of the shaft 14 to bend downward in the direction of the handle 12 in which the thumb grip 120 is located. Simultaneously pushing the finger grips 110 in a distal direction causes the half-tube 440A to slide distally, transmitting a force onto the superior aspect of the attachment ring 460, assisting the distal end of the shaft 14 to bend downward. Similarly, simultaneously applying a proximally-directed force to the finger grips 110 and a distally directed force against the thumb grip 120 causes the half-tube 400A to slide proximally and the half-tube 400B to slide distally. This will cause the distal deflection member 440A to pull the tip 16 upward, bending the distal end of the shaft 14 upward in the direction of the finger grips 110. The opposing motions of the half-tubes reduce the amount of force and longitudinal travel required to deflect the tip 16. All relative descriptions herein such as top, bottom, left, right, up, and down are with reference to the figures, and thus should not be construed in a limiting sense.

Figure 6:
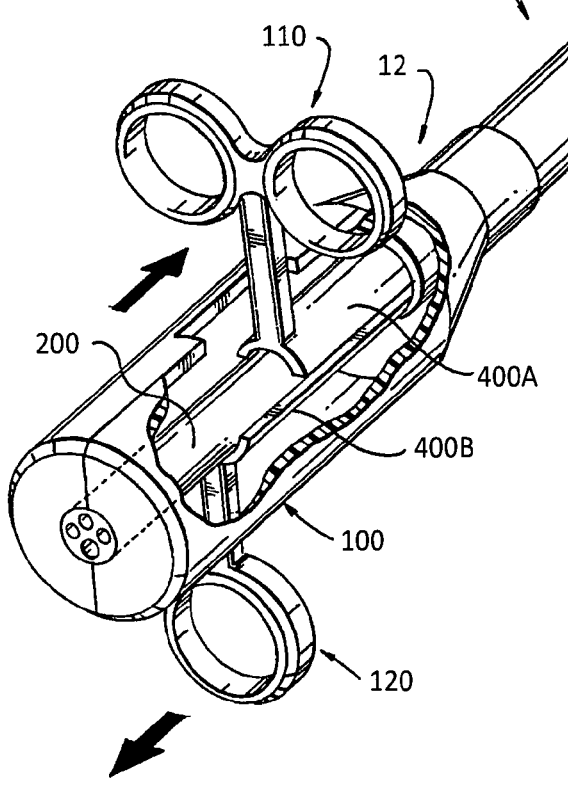
FIG. 6 shows a rigid attachment of the flat members of the deflection assembly to the attachment ring.
Figure 6:
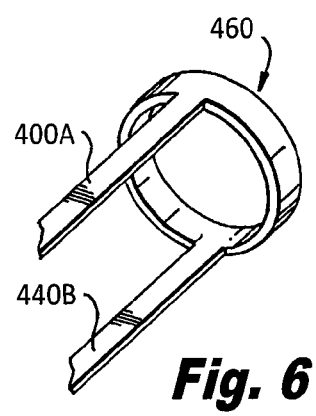
Figure 7:
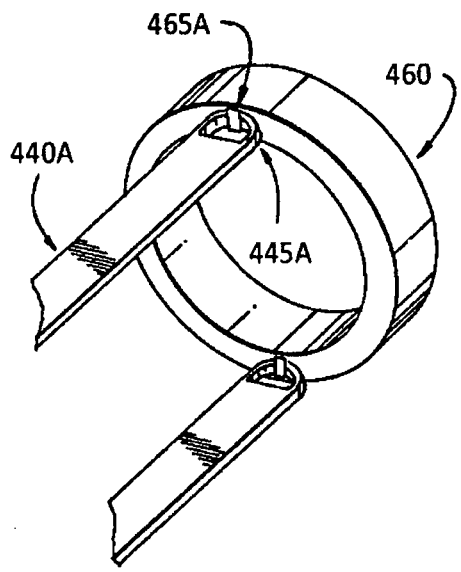
FIG. 7 shows a moveable attachment of the flat member of a deflection assembly to the attachment ring, in which the distal end of the flat member has a ring that connects to a notch formed within the attachment ring.

In one embodiment, the deflection members 440A and 440B are welded or otherwise rigidly attached to the attachment ring 460, as seen in FIG. 6. Alternatively it may be advantageous to allow some degree of angular movement at the attachment sites as the shaft 14 is deflected. This can reduce stress on the connection during deflection. One way to accomplish this is shown in FIG. 7, in which the end of the deflection member 440A is formed into a ring 445A, which then connects to a notch 465A in the attachment ring 460.

Figure 8:
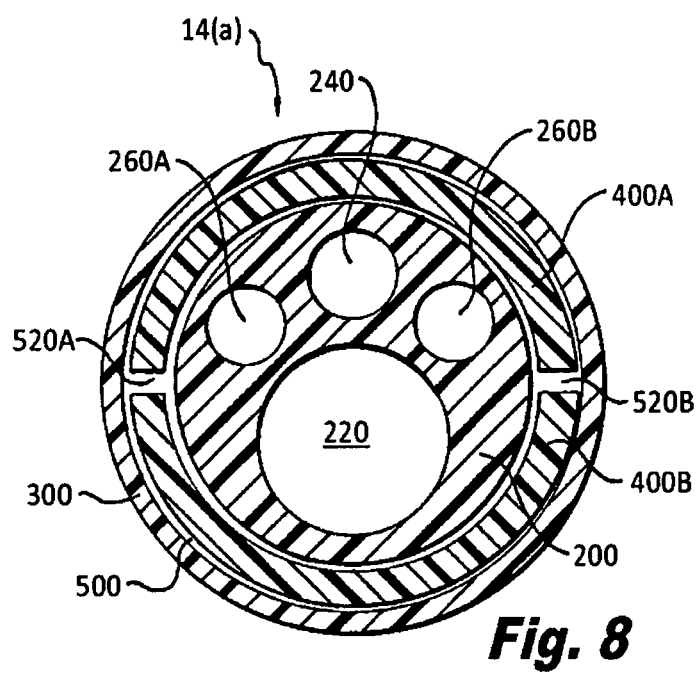
FIG. 8 is a cross-sectional view of the proximal and mid-portions of the shaft of the endoscope, showing that the half-tubes are located within the annular space between a multi-lumen inner tube and an outer tube of the shaft. The multi-lumen inner tube contains 2 channels for transmission of light, one channel for transmission of visual images, and a lumen for medical treatment.

A cross-sectional view of the portion of the shaft 14 of the instrument that contains the half-tubes 400A and 400B is represented by FIG. 8. The reference 14(a) in FIG. 8 refers to the general location identified as "a" in FIG. 1. In the disclosed embodiment, the half-tubes 400A and 400B are nearly semicircular in cross-sectional dimension, and are located in the annular space 500 between the inner wall of the outer tube 300, and the outer wall of the multi-lumen inner tube 200. In order to facilitate opposing movement between the half-tubes 400A and 400B, there are small gaps 520A and 520B between the opposing half-tubes 400A and 400B, to allow their independent motion. Because the deflection assembly 480 is not attached to either the multi-lumen inner tube 200 or the outer tube 300, the two half-tubes 400A and 400B can also rotate within the annular space 500 about the axis of the multi-lumen inner tube 200. This allows the operator to change the angle of deflection of the tip through a range of angles from 0 degrees. The independence of the deflection assembly allows it to be rotated with the tip 16 fully extended or flexed without applying any axial torsion to the multi-lumen inner tube 200. The tip 16 can thus sweep through a field from 0 to 180 degrees without changing the rotational orientation of an attached lens or camera. This helps to maintain a constant orientation of the displayed image transmitted from the tip of the instrument.

In the disclosed embodiment, within the multi-lumen inner tube 200 are several channels. Channel 240 is designed to carry the fiberoptic or electronic cable that transmits an image from the tip 16 of the instrument. Channels 260A and 260B are designed to carry the optical fibers for illuminating the area in the vicinity of the tip 16 of the instrument. These fibers can be made from plastic for improved flexibility and lower cost. Channels 240, 260A and 260B have diameters that can range in size from about 0.8 mm to about 1.2 mm. The lumen 220 is designed to carry out tissue sampling or treatment at the tip 16 of the instrument, and is generally larger than the other channels, ranging in diameter from about 1.0 mm to about 5 mm. In the disclosed embodiment, the lumen 220 is about 1.2 mm in diameter. Its size will depend on whether it must accommodate surgical instruments, or whether it is only needed to deliver drugs, or deliver or withdraw fluids or gases. Moreover, the sizes of the lumens 220, 240, 260 will depend on the overall size of the shaft 14, which in turn depends on the anatomical region for which the device is designed. It will be apparent to those skilled in the art that there are numerous possible combinations, configurations and shapes of the functional channels within the multi-lumen inner tube 200, none of which will detract from the scope of the claimed invention.

Figure 9:
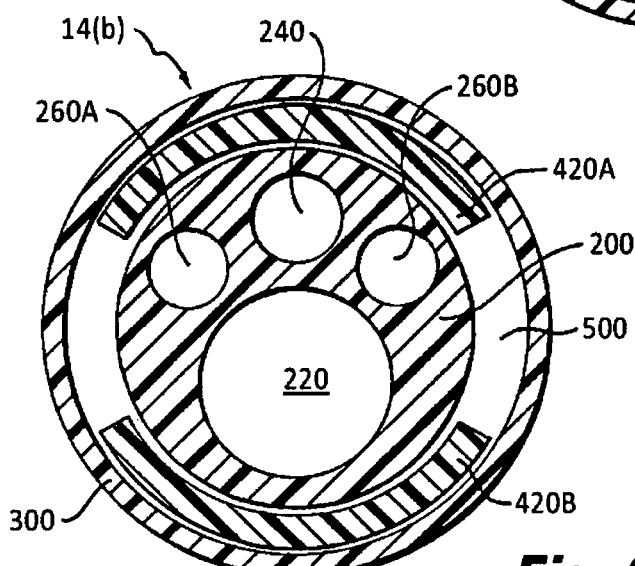
FIG. 9 is a cross-sectional view of the shaft of the endoscope near the distal end of the shaft, at a point where the half-tubes are transitioning (narrowing) within the annular space to flat members.
Figure 10:
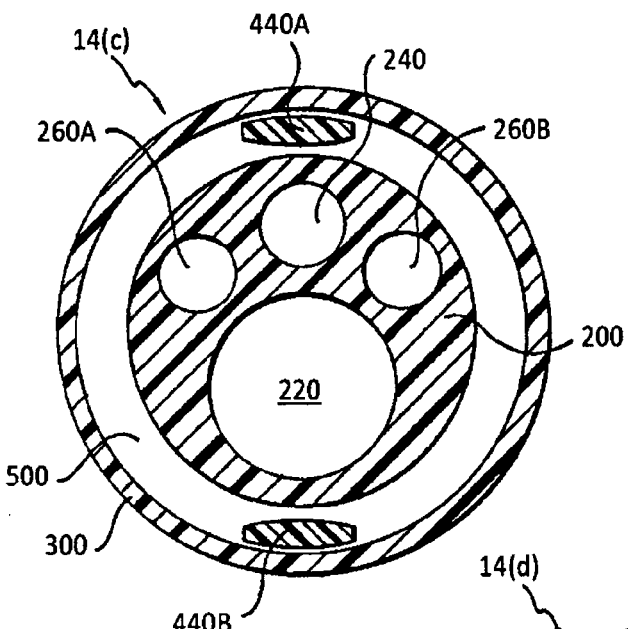
FIG. 10 is a cross-sectional view of the shaft of the endoscope near the distal end of the shaft, where the flat members are located within the annular space.
Figure 11:
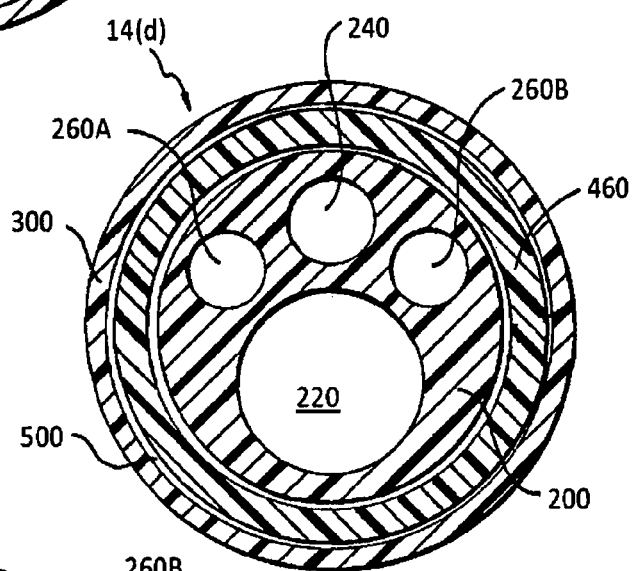
FIG. 11 is a cross-sectional view of the shaft of the endoscope near the distal end of the shaft, through the attachment ring that forms the end of the deflection assembly, and which is located within the annular space of the shaft of the endoscope.

FIG. 9 represents a cross-sectional view of the shaft 14 of the instrument at a point where the transition structures 420A and 420B are located, corresponding generally to position "b" in FIG. 1 as indicated by the reference 14(b) in FIG. 9. The curvature of the transition structures 420A and 420B becomes progressively shallower as the transition structure extends toward the distal end of the instrument. The result is that the volume of the annular space 500 that is occupied by the transition structures 420A and 420B becomes progressively smaller. In FIG. 10, the deflection members 440A and 440B are seen as this is a cross-sectional view near the distal end of the shaft 14 of the instrument taken generally at position "c" in FIG. 1 as indicated by reference 14(c) in FIG. 10. The deflection members 440A and 440B are now sufficiently flat and narrow to be flexible in a vertical direction, causing the shaft 14 of the instrument to bend in a vertical direction either upward or downward. The flattened cross-sectional contour of the deflection members 440A and 440B helps to enforce deflection of the tip 16 in a single plane. The deflection assembly 480 terminates near the tip 16 of the instrument at the attachment ring 460. A cross-sectional view of the shaft 14 of the instrument at this location is given by FIG. 11, which is generally taken at position "d" in FIG. 1 as indicated by reference 14(d) in FIG. 11. As shown, the attachment ring 460 is present circumferentially within the annular space 500.

Figure 12:
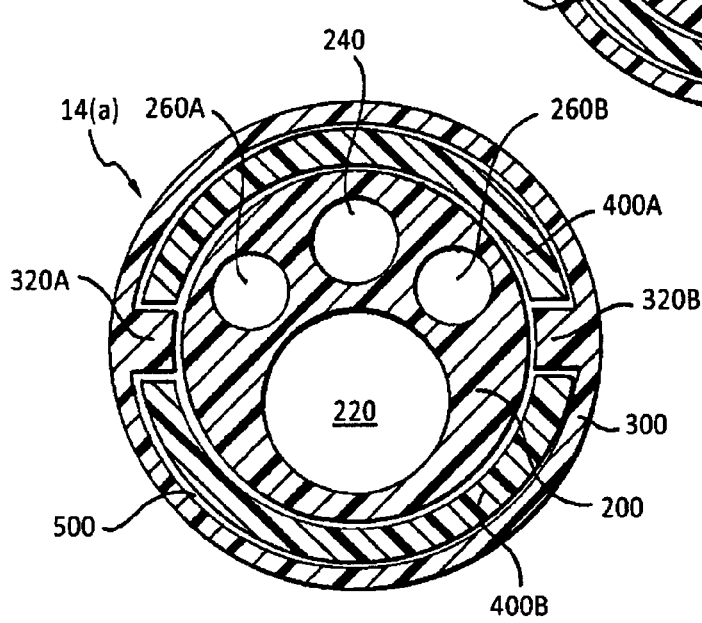
FIG. 12 is an alternative construction of the shaft of the endoscope, in which two ribs are formed from the inner wall of the outer tube, and are located in the gaps between the two half-tubes.

In an alternative embodiment, the half-tubes 400A and 400B are prevented from rotating independently of the outer tube 300. An example of this is shown in FIG. 12, in which, as with FIG. 8, the reference 14(a) indicates generally the location identified as "a" in FIG. 1. In this embodiment shown in FIG. 12, ribs 320A and 320B now occupy the gaps 520A and 520B that were shown in FIG. 8. These ribs may be either attached to or formed from the inner wall of the outer tube 300. This embodiment has the advantage of keeping the half-tubes 400A and 400B from overlapping one another when a rotational force is applied to the deflection assembly 480. It also aids in the torsional properties of the combined inner tube/half-tubes structure, and reduces the overall friction during rotation by eliminating the friction of the half-tubes on the outer shaft during rotation. Independent motion between the deflection assembly 480 and the multi-lumen inner tube 200 is preserved, thus continuing to prevent rotational forces from being transferred to a camera within the multi-lumen inner tube 200 positioned at the tip 16 of the instrument.

Figure 13:
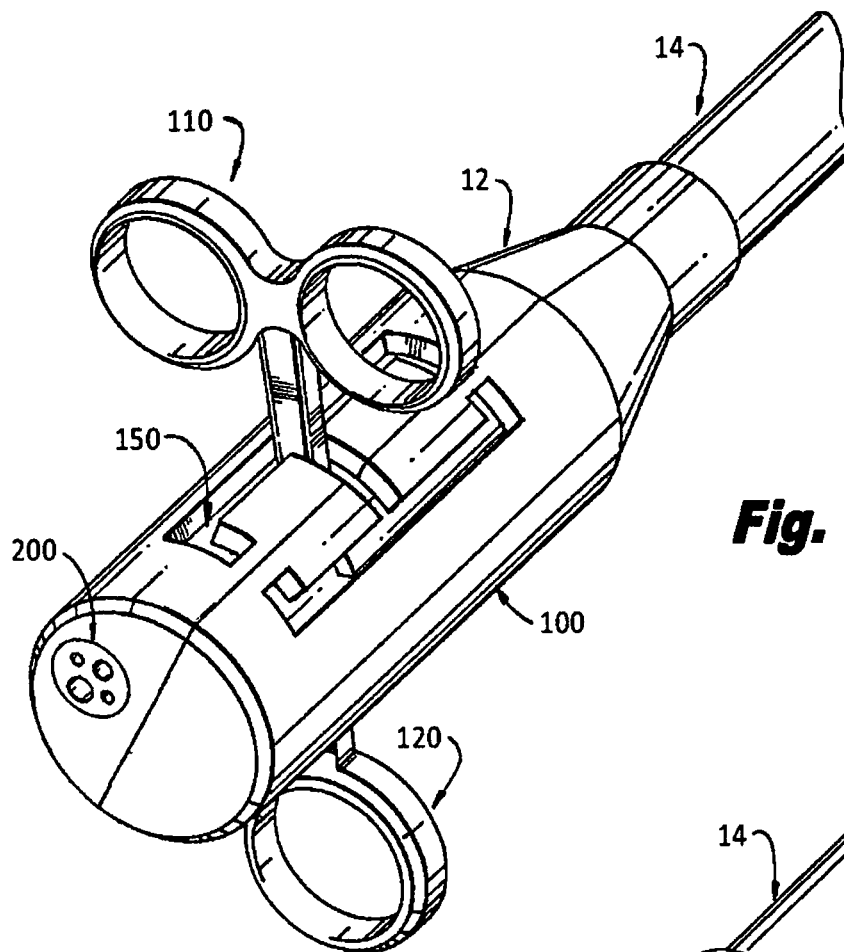
FIG. 13 is a perspective view of the handle of the endoscope shown in FIG. 1, depicting longitudinal and transverse slide tracks that guide the movement of the finger grips controlling the deflection members.

Movement of the deflection assembly is guided by a slide track system 150 in the housing 100 of the handle 12 of the instrument, as shown in FIG. 13. The finger grips 110 and thumb grip 120 are guided by separate, preferably symmetrical slide track systems. These are narrow longitudinal and transverse slots that guide the proximal and distal translation of the half-tubes 400A and 400B, as well as the rotational translation of the deflection assembly 480. Proximal translation of one half-tube and distal translation of the other half-tube results in the bending of the tip 16 of the instrument in the direction of the proximally translated half-tube. Translation of both half-tubes 400A and 400B in the same direction moves the entire deflection assembly proximally or distally along the shaft 14 of the instrument, thus varying the point along the shaft at which bending occurs. In an embodiment of the invention, the proximal ends of the half-tubes 400A and 400B are linked within the handle 12, facilitating either their unidirectional motion or opposing motion, and reducing the number of finger grips or knobs required for operating the instrument.

Also shown in FIG. 13 is an alternative embodiment of the location of the proximal end of the multi-lumen inner tube 200. In this embodiment, the multi-lumen inner tube 200 is off-set within the handle 12, moving the access to the channels away from the hand that grips the handle 12. This improves access for connecting to or using the channels within the multi-lumen tube when the handle and controls are operated with one hand.

Figure 14:
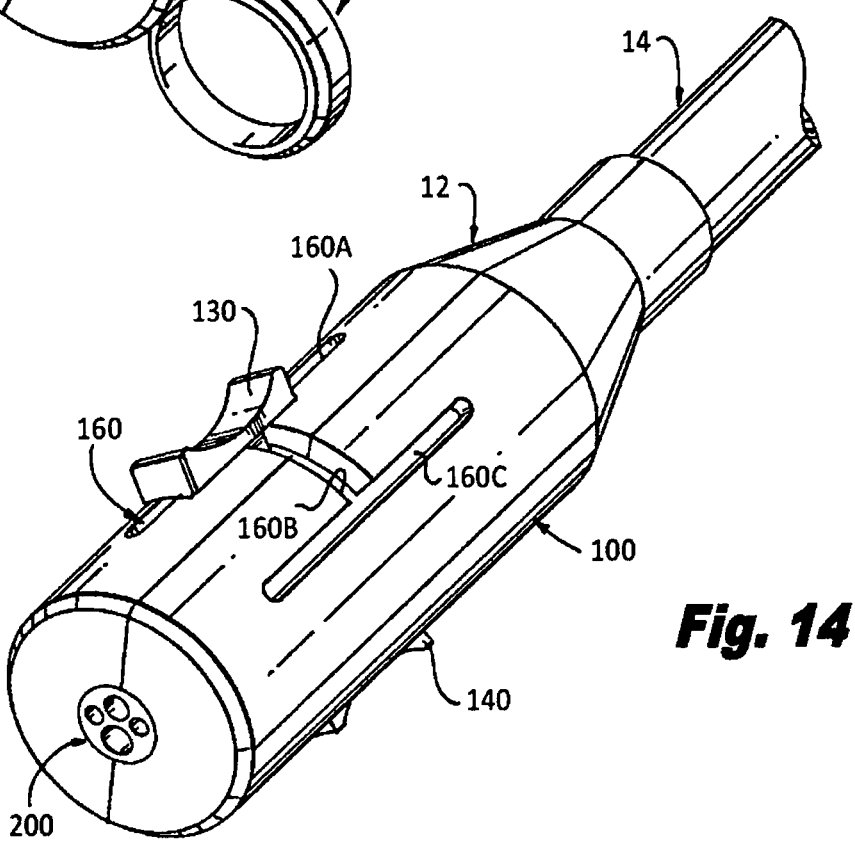
FIG. 14 is a perspective view of the handle of the endoscope shown in FIG. 1, depicting an alternative arrangement in which slide tracks guide the movement of knobs controlling the deflection members.

An alternative embodiment of the design of the handle 12 is shown in FIG. 14. In this case the slide track system 160 incorporates two proximal-distal slide tracks 160A and 160C at different rotational orientations, separated by a single rotational slide track 160B. A symmetrical set of slide tracks (not shown) can be located on the opposing side of the handle 12. FIG. 14 also shows an alternative embodiment of the design of the handle 12 incorporating knobs instead of finger and thumb grips for the manipulation of the deflection assembly 480. A further embodiment includes an interlocking ratchet feature connected to the finger grips or knobs that causes the deflection position to be temporarily fixed. It will be readily apparent to one skilled in the art that numerous structures are possible both for guiding the directional movement of the deflection assembly 480 and for providing contact points between the half-tubes 400A and 400B and the operator's hands to manually actuate the deflection assembly; and that such modifications may be made without departing from the scope of the invention.

Further embodiments may include two concentric deflection assemblies, allowing the operator to bend the distal end of the instrument in two planes simultaneously. Moreover, the ability to slide each deflection assembly independently allows the operator to cause the shaft 14 of the instrument to bend at two locations simultaneously (e.g., an 'elbow and wrist' articulation).

Other embodiments may include more than one pair of deflection members. For example, a set of three deflection members will permit bending of the instrument tip at angles 120 degrees apart; four deflection members will permit bending of the instrument tip at angles 90 degrees apart. Additional deflection members may be added subject to the condition that the curved portion of each deflection assembly remains sufficiently rigid to retain the unique benefits of the invention.

A number of embodiments of a deflectable scope have been described. These embodiments are exemplary and not limiting. Various changes and combinations are possible and are within this disclosure even if not specifically described. The size of the disclosed instrument embodiments can be varied as well, and such variations also are within this disclosure.

What is claimed is:

1. A medical instrument, comprising:
    a handle;
    a flexible shaft extending distally from the handle, the shaft comprising an outer elongated member and an inner elongated member disposed within at least a portion of the outer elongated member, the arrangement of the outer and inner members defining a space therebetween; and
    a deflection assembly disposed within the space and being manipulatable by a user of the instrument to deflect a distal portion of the shaft in at least one of two possible directions off a longitudinal axis running the length of the shaft,
    wherein the deflection assembly comprises: (i) a proximal portion having a curved profile concentric with one of the inner and outer members, (ii) a distal portion having a substantially flat profile, and (iii) a tapering portion between the proximal portion and the distal portion, the tapering portion comprising a curved profile tapering in a distal direction proximate to a distal end of the shaft.

2. The medical instrument of claim 1, wherein the deflection assembly comprises at least two elements, each of the at least two elements having (i) a proximal portion having a curved profile concentric with one of the inner and outer members, (ii) a distal portion having a substantially flat profile, and (iii) a tapering portion between the proximal portion and the distal portion, the tapering portion comprising a curved profile tapering in a distal direction proximate to a distal end of the shaft.

3. The medical instrument of claim 2, wherein a proximal end of each of the at least two elements comprises a grip manipulatable by a user of the instrument to deflect a distal portion of the shaft.

4. The medical instrument of claim 3, wherein each grip is integrally formed with each of the at least two elements.

5. The medical instrument of claim 3, wherein each grip is connected to each of the at least two elements.

6. The medical instrument of claim 1, wherein the deflection assembly comprises at least two half-tubes, each of the at least two half tubes including a transition structure.

7. The medical instrument of claim 6, wherein the deflection assembly comprises a deflection member extending distally from each of the transition structures.

8. The medical instrument of claim 7, wherein the deflection members are connected to an attachment ring at a distal end of the shaft.

9. The medical instrument of claim 1, wherein the outer elongated member comprises at least one rib to prevent the deflection assembly from rotating independently of the outer elongated member.

10. The medical instrument of claim 1, wherein inner elongated member comprises at least one lumen extending from a proximal end disposed in the handle to a distal end of the shaft.

11. The medical instrument of claim 1, wherein the deflection assembly can be manipulated independent of the shaft.

12. The medical instrument of claim 1, wherein the outer elongated member comprises a lubricated coating.

13. The medical instrument of claim 1, wherein the outer elongated member comprises a drug coating.

14. A medical instrument, comprising:
    a handle;
    a flexible shaft extending distally from the handle, the shaft comprising an outer elongated member and an inner elongated member disposed within at least a portion of the outer elongated member, the arrangement of the outer and inner members defining a space therebetween; and
    a deflection assembly disposed within the space and being manipulatable by a user of the instrument to deflect a distal portion of the shaft, the deflection assembly comprising at least two half-tubes, each of the at least two half tubes including a deflection member connected to an attachment ring at a distal end of the shaft;
    wherein each of the at least two half-tubes comprises: (i) a proximal portion having a curved profile concentric with one of the inner and outer members, (ii) a distal portion having a substantially flat profile, and (iii) a tapering portion between the proximal portion and the distal portion, the tapering portion comprising a curved profile tapering in a distal direction proximate to a distal end of the shaft.

15. The medical instrument of claim 14, wherein the deflection assembly can be manipulated independent of the shaft.

16. The medical instrument of claim 14, wherein a proximal end of each of the at least two half-tubes comprises a grip manipulatable by a user of the instrument to deflect and/or rotate the distal portion of the shaft.

17. The medical instrument of claim 14, wherein inner elongated member comprises at least one lumen extending from a proximal end disposed in the handle to a distal end of the shaft.

18. The medical instrument of claim 14, wherein the outer elongated member comprises at least one rib to prevent the deflection assembly from rotating independently of the outer elongated member.

19. The medical instrument of claim 14, wherein the deflection member includes two deflection members, each deflection member corresponding to and fixedly connected directly to one of the at least two half-tubes.

20. The medical instrument of claim 14, wherein the two half-tubes define a pair of gaps extending longitudinally.

* * * * *